US007919290B2

(12) United States Patent
Offerman et al.

(10) Patent No.: US 7,919,290 B2
(45) Date of Patent: *Apr. 5, 2011

(54) BIO-RECYCLING OF CARBON DIOXIDE EMITTED FROM POWER PLANTS

(76) Inventors: John D. Offerman, Orono, MN (US); Hugh McTavish, Birchwood, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/380,121

(22) Filed: Feb. 24, 2009

(65) Prior Publication Data

US 2009/0162914 A1    Jun. 25, 2009

Related U.S. Application Data

(62) Division of application No. 11/821,935, filed on Jun. 26, 2007, now Pat. No. 7,608,439.

(60) Provisional application No. 60/816,510, filed on Jun. 26, 2006.

(51) Int. Cl.
| | | |
|---|---|---|
| C12P 5/02 | (2006.01) | |
| C12P 3/00 | (2006.01) | |
| C12P 7/04 | (2006.01) | |
| C12P 7/06 | (2006.01) | |
| C12P 7/16 | (2006.01) | |

(52) U.S. Cl. ........ 435/161; 435/157; 435/160; 435/167; 435/168; 435/252.1; 435/289.1; 435/303.2

(58) Field of Classification Search ........................ None
See application file for complete search history.

(56) References Cited

U.S. PATENT DOCUMENTS

| | | | |
|---|---|---|---|
| 4,235,801 | A | 11/1980 | Bhasin |
| 4,333,852 | A | 6/1982 | Warren |
| 4,492,772 | A | 1/1985 | Ball |
| 4,571,384 | A | 2/1986 | Morita |
| 4,675,344 | A | 6/1987 | Conway |
| 4,749,724 | A | 6/1988 | Quarderer |
| 4,752,623 | A | 6/1988 | Stevens |
| 4,758,600 | A | 7/1988 | Arimitsu |
| 4,762,858 | A | 8/1988 | Hucul |
| 4,921,799 | A | 5/1990 | Kitaura |
| 5,185,079 | A | 2/1993 | Dague |
| 5,543,049 | A | 8/1996 | Hogen |
| 5,620,893 | A | 4/1997 | Hogen |
| 5,667,673 | A | 9/1997 | Hogen |
| 5,821,111 | A | 10/1998 | Grady |
| 6,248,796 | B1 | 6/2001 | Jackson |
| 6,299,774 | B1 | 10/2001 | Ainsworth |
| 6,569,332 | B2 | 5/2003 | Ainsworth |
| 6,601,543 | B2 | 8/2003 | Rautenbach |
| 6,664,101 | B2 | 12/2003 | Wild |
| 6,802,974 | B2 | 10/2004 | Rebholz |
| 6,824,682 | B2 | 11/2004 | Branson |
| 7,309,592 | B2 | 12/2007 | Offerman |
| 2005/0113467 | A1 | 5/2005 | Branson |

FOREIGN PATENT DOCUMENTS

| | | |
|---|---|---|
| EP | 0 235 886 A2 | 9/1987 |
| EP | 0235886 A2 | 9/1987 |
| EP | 0253 540 A1 | 1/1988 |
| EP | 0253540 A1 | 1/1988 |
| EP | 1574581 A2 | 9/2005 |
| WO | WO 03/042117 A1 | 5/2003 |
| WO | WO 2006/108532 | 10/2006 |

OTHER PUBLICATIONS

Bao, J. et al., 2003, A highly active K-Co-Mo/C catalyst for mixed alcohol synthesis from CO and H2. Chem. Commun. 2003:746-747.
Beretta, A. et al., 1996, Production of methanol and isobutyl alcohol mixtures over double-bed cesium-promoted Cu/ZnO/Cr2O3 and ZnO/Cr2O3 catalysts. Ind. Eng. Chem. Res. 35:1534-1542.
Beretta, A. et al., 1998, Development of a process for higher alcohol production via synthesis gas. Ind. Eng. Chem. Res. 37:3896-3908.
Bian, G.-Z. et al., 1998, Mixed alcohol synthesis from syngas on sulfide K-Mo-based catalysts: influence of support acidity. Ind. Eng. Chem. Res. 37:1736-1743.
Bredwell, M.D. et al., 1999, Reactor design issues for synthesis gas fermentations. Biotechnol. Prog. 15:834-844.
Breman, B.B. et al., 1995, Kinetics of the gas-slurry methanol-higher alcohol synthesis from CO/CO2/H2 over a Cs-Cu/ZnO/Al2O3 catalyst, including simultaneous formation of methyl esters and hydrocarbons. Catalysis Today 24:5-14.
Burcham, M.M. et al., 1998, Higher alcohol synthesis over double bed Cs-Cu/ZnO/Cr2O3 catalysts: optimizing the yields of 2-methyl-1-propanol (isobutanol). Ind. Eng. Chem. Res. 37:4657-4668.
Ehwald, H. et al., 1991, A bicomponent catalyst for the selective formation of ethanol from synthesis gas. Applied Catalysis 76: 153-169.
Iranmahboob, J. et al., 2003, Dispersion of alkali on the surface of Co-MoS2/clay catalyst: a comparison of K and Cs as a promoter for synthesis of alcohol. Applied Catalysis A: General 247:207-218.
Klasson, K.T. et al., 1992, Biological conversion of synthesis gas into fuels. Int. J. Hydrogen Energy 17:281-288.
Klasson, K.T. et al., 1993, Biological conversion of coal and coal-derived synthesis gas. Fuel 72:1673-1678.
Matsuzaki, T. et al., 1993, Effect of transtion metals on oxygenates formation from syngas over Co/SiO2. Applied Catalysis A: General 105: 159-184.
Pereira, E.B. et al., 1993, Alcohol synthesis from syngas over nickel catalysts: effect of copper and lithium addition. Applied Catalysis A: General 103:291-309.

(Continued)

Primary Examiner — Herbert J. Lilling
(74) Attorney, Agent, or Firm — Hugh McTavish

(57) ABSTRACT

The invention provides a method to decrease emission of carbon dioxide from combustion of fossil fuels or other hydrocarbons and to enhance the efficiency of methane production from anaerobic biodigesters. The invention involves feeding carbon dioxide from the exhaust gas of hydrocarbon fuel combustion to an anaerobic biodigester where biomass is anaerobically fermented to produce methane. Carbon dioxide is an electron acceptor for anaerobic fermentation, and thus some of the carbon dioxide is reduced to methane, which can again be used for fuel. In this way, at least a portion of the exhaust gas $CO_2$ is recycled to form fuel methane instead of being released into the atmosphere. Thus, the net $CO_2$ emission from burning a given amount of fossil fuel is decreased. Adding carbon dioxide to an anaerobic fermentation also increases the efficiency and amount of methane production in the fermentation.

7 Claims, 5 Drawing Sheets

OTHER PUBLICATIONS

Smith, K.J., C.-W. Young, R.G. Herman, and K. Klier, 1991, Development of a kinetic model for alcohol synthesis over a cesium-promoted Cu/ZnO catalyst. Ind. Eng. Chem. Res. 30:61-71.

Stiles, A.B. et al., 1991, Catalytic conversion of synthesis gas to methanol and other oxygenated products. Ind. Eng. Chem. Res. 30:811-821.

Sun, X and G.W. Roberts, 2003, Synthesis of higher alcohols in a slurry reactor with cesium-promoted zinc chromite catalyst in decahydronaphthalene. Applied Catalysis A: General 247:133-142.

Suvajittanont, W. et al., 2003, Potential of biogas recirculation to enhance biomass accumulation on supporting media. Bioreseource Technology 88:157-162.

Worden, R.M. et al., 1991, Production of butanol and ethanol from synthesis gas via fermentation. Fuel 70: 615-619.

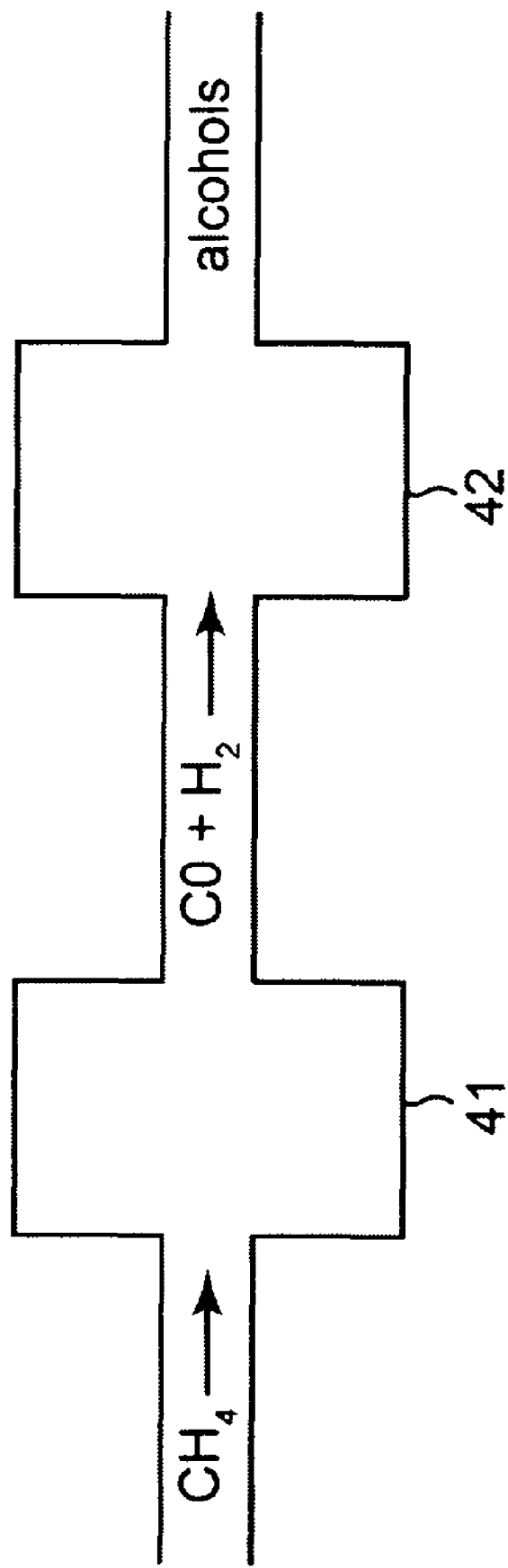

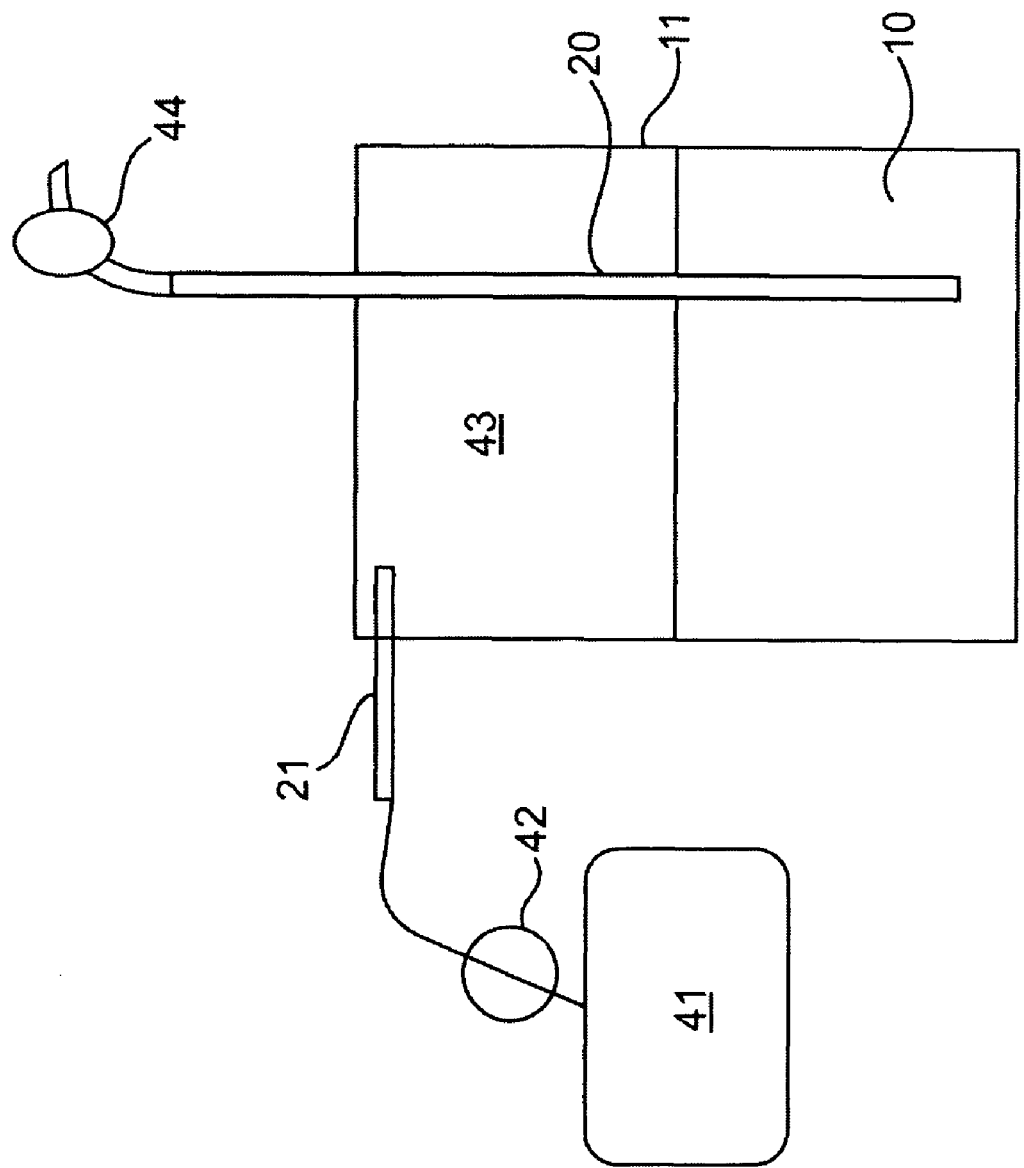

BIO-RECYCLING OF CARBON DIOXIDE EMITTED FROM POWER PLANTS

This application is a divisional of U.S. utility patent application Ser. No. 11/821,935, filed Jun. 26, 2007, now U.S. Pat. No. 7,608,439, which claims priority from U.S. provisional patent application Ser. No. 60/816,510, filed Jun. 26, 2006.

BACKGROUND

Carbon dioxide is a greenhouse gas whose concentration is increasing in the atmosphere due to combustion of fossil fuels. Carbon dioxide absorbs infrared radiation and thus traps heat in the atmosphere. In this respect it acts like the glass walls of a greenhouse, and hence it is referred to as a greenhouse gas. Since $CO_2$ traps heat in the atmosphere, the increasing carbon dioxide concentration in the atmosphere is altering our climate by increasing global temperatures and altering rain and snowfall patterns. This is likely to cause widespread ecological damage, species extinction, flooding of low-lying coastal areas, and harm agriculture in certain areas.

To avoid a runaway greenhouse effect, humanity will need to reduce fossil fuel use, increase use of renewable energy that produces no net greenhouse gas emissions, and decrease carbon dioxide release from fossil fuel burning. Methods to decrease $CO_2$ release from fossil fuel use, increase energy yield from fossil fuel combustion, or increase the yield of renewable energy are needed.

SUMMARY OF THE INVENTION

The invention provides a method to decrease emission of carbon dioxide from combustion of fossil fuels or other hydrocarbons and to enhance the efficiency of methane production from anaerobic biodigesters. The invention involves feeding carbon dioxide from the exhaust gas of hydrocarbon fuel combustion to an anaerobic biodigester where biomass is anaerobically fermented to produce methane. Carbon dioxide is an electron acceptor for anaerobic fermentation, and thus some of the carbon dioxide is reduced to methane, which can again be used for fuel. In this way, at least a portion of the exhaust gas $CO_2$ is recycled to form fuel methane instead of being released into the atmosphere. Thus, the net $CO_2$ emission from burning a given amount of fossil fuel is decreased.

Furthermore, feeding exhaust gas $CO_2$ to the anaerobic biodigester increases the efficiency of the biodigester and the yield of methane because $CO_2$ is often the limiting substrate in anaerobic fermentations. Since methane produced from anaerobic fermentation of biomass is a renewable form of energy, feeding exhaust gas $CO_2$ to an anaerobic biodigester also increases the yield of a renewable form of energy.

In anaerobic biodigesters, anaerobic microorganisms ferment reduced carbon substrates to other products. For instance, some organisms transform hexose sugars to ethanol and $CO_2$. Other common fermentation products include lactic acid, acetic acid, butyric acid, $H_2$, and methane. Many fermentation products are themselves substrates for fermentation by other anaerobic microorganisms. However, two fermentation products cannot be further fermented—methane and $CO_2$, the most reduced and most oxidized carbon compounds. Thus, all anaerobic decomposition can ultimately lead to methane and carbon dioxide.

Organisms that produce methane are called methanogens. Methanogens can produce methane from acetate by the reaction acetate+$H_2O$-->methane+$HCO_3^-$. In what is probably a more important reaction though, methanogens can also produce methane from hydrogen and $CO_2$ by the reaction $4H_2$+$HCO_3^-$+$H^+$-->$CH_4$+$3H_2O$. The hydrogen for methanogenesis from carbon dioxide in nature comes from fermentation of reduced carbon substrates. But hydrogen gas can also be supplied directly to a fermenter for methane production.

Thus, in addition to being a fermentation product, $CO_2$ is a crucial electron acceptor for methane production from hydrogen. Anaerobic fermentation generally and methane production specifically are slowed when the carbon dioxide concentration is too low. Carbon dioxide is often a limiting factor in anaerobic methanogenesis.

The invention involves feeding a combustion exhaust gas that is rich in $CO_2$ into an anaerobic digester to enhance methane production in the digester. The $CO_2$ increases methane production from the digester, which means that a portion of the $CO_2$ is reduced to methane, and carbon dioxide emissions from fossil fuel burning are reduced. By increasing methane production from anaerobic digestion of biomass, the method also increases the yield of a renewable form of energy.

If hydrogen gas is the reduced substrate for the anaerobic digester, all the fed $CO_2$ can be converted to methane. The hydrogen gas can be produced renewably, such as by using wind energy to produce electricity for electrolysis of water. This in effect recycles the carbon dioxide as it is burned. If the methane produced by the process is also burned, the $CO_2$ exhaust can be captured and reduced to methane with hydrogen again, and so on indefinitely.

The biogas methane can be burned for energy to produce heat or electricity. Alternatively, it may be converted to a liquid fuel by first converting it to a syngas containing CO and $H_2$, and then contacting the CO and $H_2$ with a catalyst under high pressure and heat to form alcohol. This is known as a Fischer-Tropsch type process. Thus, one motivation for using hydrogen to reduce combustion exhaust $CO_2$ to methane by the present process would be to further convert the methane to alcohol and thereby convert hydrogen gas to a liquid fuel that is more easily transportable and that, unlike hydrogen, has a present market as an automotive fuel.

It should be noted that methanogenic microorganisms are very sensitive to oxygen. Therefore, it is important to eliminate oxygen from the exhaust gas $CO_2$ before feeding the exhaust gas $CO_2$ to an anaerobic fermenter.

Thus, one embodiment of the invention provides a method of producing methane comprising: (a) collecting combustion exhaust gas from a hydrocarbon fuel combustion process; (b) separating $O_2$ from $CO_2$ in the exhaust gas to generate a $CO_2$-rich anaerobic exhaust gas fraction; (c) feeding the $CO_2$-rich anaerobic exhaust gas fraction to a fermentation mixture containing methanogenic microorganisms; (d) feeding a reduced substrate selected from the group consisting of $H_2$ and organic material and a combination thereof, to the fermentation mixture; and (e) producing a biogas comprising methane in the fermentation mixture by the action of methanogenic microorganisms; wherein feeding the $CO_2$-rich anaerobic exhaust gas fraction to the fermentation mixture increases methane production in the fermentation mixture.

Another embodiment of the invention provides a method of producing alcohol comprising: (a) fermenting organic material in a fermentation mixture to a biogas comprising methane and $CO_2$; (b) fractionating the biogas into a methane-rich fraction and a $CO_2$-rich fraction; (c) converting at least a portion of the methane-rich fraction to synthesis gas comprising CO and $H_2$; (d) contacting the synthesis gas with a catalyst to produce alcohol; and (e) recirculating at least a portion of the $CO_2$-rich fraction to the fermentation mixture to enhance biogas methane production.

BRIEF DESCRIPTION OF THE DRAWINGS

FIG. 4 shows steps to convert a biogas to alcohol.

FIG. 5 shows operation of a biodigester producing a methane-containing biogas.

DETAILED DESCRIPTION

Definitions

Figure 1:
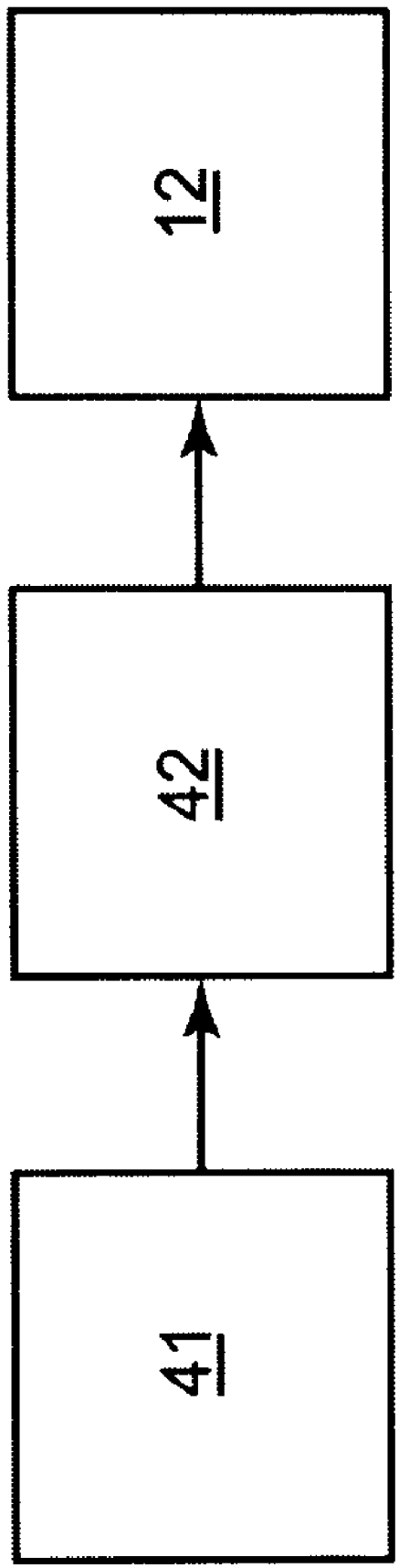
FIG. 1 is a schematic diagram showing combustion of hydrocarbons and production of a $CO_2$-rich anaerobic combustion exhaust gas.

"Biogas" as used herein refers to a gas produced by the fermentative anaerobic metabolism of microorganisms. The biogases described herein contain methane and typically contain carbon dioxide as their major constituents.

The term "fermenting" organic material as used herein refers to digestion of the organic material by microorganisms using anaerobic respiration, or, if specified, using aerobic respiration.

The term "partially oxidizing" as used herein refers to incomplete oxidation of a reduced substrate by reaction with oxygen or another oxidizing agent. An example is conversion of methane to a more oxidized compound other than carbon dioxide, e.g., methanol or carbon monoxide. In a particular embodiment, partially oxidizing a biogas involves reacting methane with $O_2$ to produce CO and $H_2$. "Partially oxidizing" the biogas includes partially oxidizing all of the biogas and partially oxidizing a portion of the biogas.

The term "sulfhydryls" as used herein refers to SH groups or to compounds having one or more SH groups. The term "sulfhydryls" includes, e.g., hydrogen sulfide, methanethiol, ethanethiol, and 2-mercaptoethanol.

The term "sulfided, nanosized transition metal catalyst" refers to a catalyst composed primarily of a transition metal or a combination of transition metals, where the particles have a mean particle diameter less than 200 nm, preferably less than 100 nm, and where the metal is sulfided.

The term "volatile organic acid" refers to a compound having a COOH group and containing 6 or fewer carbon atoms. It includes formic acid, acetic acid, propionic acid, and butyric acid.

The terms "$C_2$+ alcohols" and "$C_3$+ alcohols" refer to alcohols having, respectively, two or more and three or more carbons.

The terms "alcohol" and "purified alcohol" produced by the methods of the invention include mixtures of alcohols and mixtures containing alcohols and other components, including in some cases water, aldehydes, ketones, ethers, esters, organic acids, and acid anhydrides. Preferably the alcohol and purified alcohol products of the methods of the invention consist of greater than 50%, more preferably greater than 60%, more preferably greater than 70%, more preferably greater than 80%, more preferably greater than 90%, and more preferably still greater than 95% by weight alcohols.

The term "volatile organics" refers to the mass of material in a biomass that is liquid or solid after drying at 105° C. and gasified after heating to 550° C. in air.

The term "anaerobic digester" as used herein refers to a device adapted to contain an anaerobic fermentation mixture that includes anaerobic microorganisms and a substrate for the anaerobic microorganisms.

DESCRIPTION

Some important fermentation reactions are shown below.

| | |
|---|---|
| $C_6H_{12}O_6 \rightarrow 2\ CH_3CH_2OH + 2\ CO_2$ | Hexose fermentation to ethanol |
| $4\ H_2 + 2\ CO_2 \rightarrow CH_3COOH + 2\ H_2O$ | Acetogenesis |
| $C_6H_{12}O_6 \rightarrow 2\ CH_3COOH + 2\ CO_2 + 4\ H_2$ | Hexose fermentation to acetate |
| $CH_3COOH \rightarrow CH_4 + CO_2$ | Acetate to methane and $CO_2$ |
| $CH_3(CH_2)_2COOH + 2\ H_2O \rightarrow 2\ CH_3COOH + 2\ H_2$ | Butyric acid fermentation |
| $CH_3(CH_2)_6COOH + 4\ H_2O \rightarrow 3\ CH_3COOH + 6\ H_2$ | Fatty acid fermentation |
| $4\ H_2 + CO_2 \rightarrow CH_4 + 2\ H_2O$ | Methane production from $H_2$ and $CO_2$ |

Some fermentation reactions producing hydrogen have a positive free energy change at standard conditions. But the reactions are or can be spontaneous in actual fermentation conditions because of hydrogen consumption in methanogenesis with $CO_2$ as electron acceptor, which keeps the hydrogen concentration low. Thus, these reactions depend on keeping the hydrogen concentration low due to rapid consumption of hydrogen. Examples of these coupled reactions are shown below.

| | |
|---|---|
| $2\ CH_3CH_2OH + 2\ H_2O \rightarrow 4\ H_2 + 2\ CH_3COOH$ | $\Delta G = +42$ kJ |
| $4\ H_2 + CO_2 \rightarrow CH_4 + 2\ H_2O$ | $\Delta G = -143$ kJ |
| $2\ CH_3CH_2OH + CO_2 \rightarrow CH_4 + 2\ CH_3COOH$ | $\Delta G = -101$ kJ coupled reaction |
| $2\ CH_3(CH_2)_2COOH + 4\ H_2O \rightarrow 4\ CH_3COOH + 4\ H_2$ | $\Delta G = +96$ kJ |
| $4\ H_2 + CO_2 \rightarrow CH_4 + 2\ H_2O$ | $\Delta G = -143$ kJ |
| $2\ CH_3(CH_2)_2COOH + 2\ H_2O + CO_2 \rightarrow 4\ CH_3COOH + CH_4$ | $\Delta G = -47$ kJ coupled reaction |

In these coupled reactions, one species or group of species of microorganisms performs one reaction and a second species or group of species performs the other. The term interspecies hydrogen transfer describes these interdependent reactions where hydrogen is the product of the first reaction and the substrate of the second reaction. Interspecies hydrogen transfer depends on the availability of carbon dioxide as a substrate for methanogenesis in the second reaction of each coupled reaction pair. Because of this, providing supplemental carbon dioxide by the methods of the present invention promotes methanogenesis and more efficient and complete fermentation of organic substrates.

One embodiment of the invention provides a method of producing methane comprising: (a) collecting combustion exhaust gas from a hydrocarbon fuel combustion process; (b) separating $O_2$ from $CO_2$ in the exhaust gas to generate a $CO_2$-rich anaerobic exhaust gas fraction; (c) feeding the $CO_2$-rich anaerobic exhaust gas fraction to a fermentation mixture containing methanogenic microorganisms; (d) feeding a reduced substrate selected from the group consisting of $H_2$ and organic material and a combination thereof, to the fermentation mixture; and (e) producing a biogas comprising methane in the fermentation mixture by the action of methanogenic microorganisms; wherein feeding the $CO_2$-rich anaerobic exhaust gas fraction to the fermentation mixture increases methane production in the fermentation mixture. This method is shown in FIGS. 1 and 2.

FIG. 1 is a schematic showing a hydrocarbon fuel combustion process 41 producing combustion exhaust gas 42. Oxygen is separated from $CO_2$ in the exhaust gas to produce a $CO_2$-rich anaerobic exhaust gas fraction 12.

Figure 2:
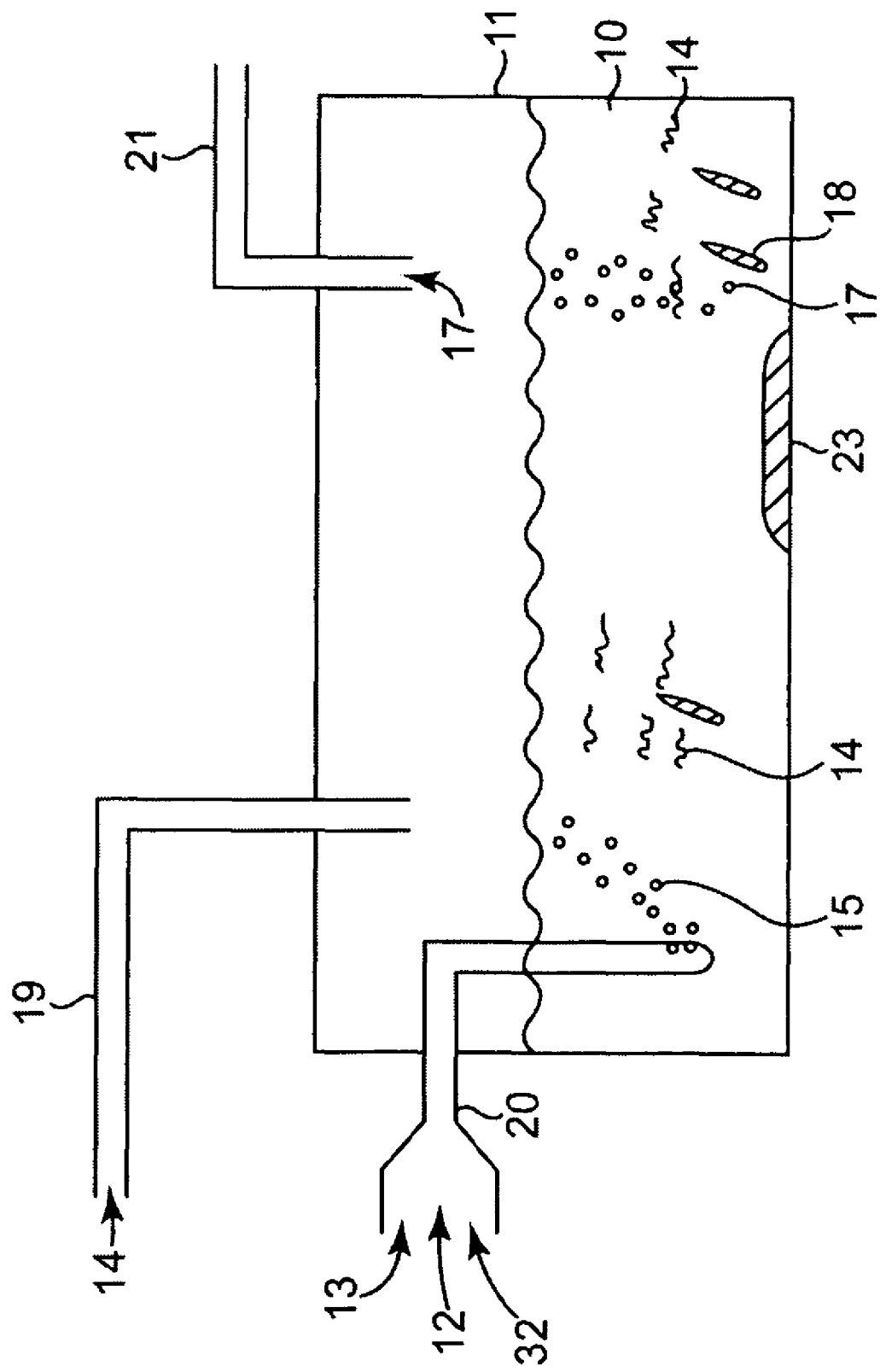
FIG. 2 shows operation of a biodigester producing a methane-containing biogas from a reduced substrate and a $CO_2$-rich anaerobic exhaust gas.

FIG. 2 shows an anaerobic digester 11 containing methanogenic microorganisms 18. A reduced carbon substrate of organic material 14 is fed into the fermentation mixture 10 in the digester 11 through pathway 19. A $CO_2$-rich anaerobic exhaust gas fraction 12 is added to the anaerobic digester, which may be through a sparger 20 to produce gas bubbles 15 in the fermentation mixture 10. By the action of methanogenic microorganisms 18 on the reduced carbon substrate 14, a biogas 17 containing methane is produced and accumulates in the headspace of the digester 11. The biogas 17 may be harvested from the digester through pathway 21. Instead of or in addition to adding a reduced carbon substrate 14, one can feed to the fermentation mixture 10 in the digester 11 $H_2$ gas 13. The hydrogen gas may be added through the same pathway 20 as the $CO_2$-rich anaerobic exhaust gas fraction to produce gas bubbles 15 to dissolve hydrogen in the anaerobic digester 11. The methanogenic microorganisms 18 use the reducing power of $H_2$ or a reduced carbon substrate to reduce $CO_2$ and produce methane in the biogas 17.

In some embodiments of the method, the reduced substrate for the microorganisms includes $H_2$. In some embodiments, it includes organic material. In some embodiments, it includes both.

The anaerobic digester will typically produce a sludge 23, which is shown in FIG. 2. This may be harvested and used as fertilizer.

Figure 3:
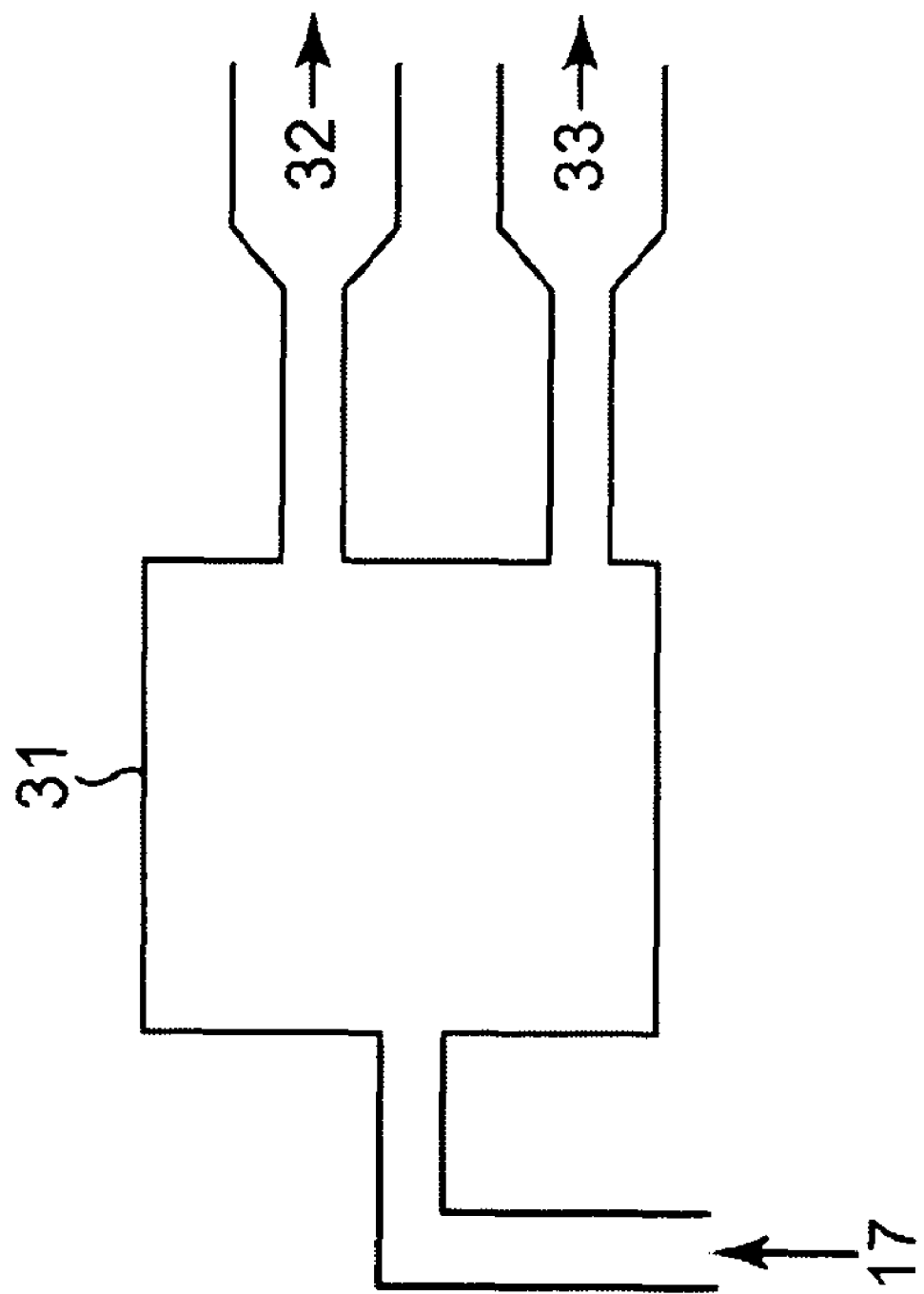
FIG. 3 is a schematic drawing showing a method of fractionating a biogas into a $CO_2$-rich fraction and a methane-rich fraction.

In the methods of the present invention, the biogas containing methane may optionally be fractionated into a methane-rich fraction and a $CO_2$-rich fraction. This is shown in FIG. 3, where a fractionation device 31 fractionates the biogas 17 into a $CO_2$ rich fraction 32 and a methane-rich fraction 33. A preferred method of fractionation is pressure swing adsorption. In this method gas is passed over a bed of adsorbent material that has selective affinity for one or more of the gases in a mixture. For instance, the adsorbent may have low affinity for methane and high affinity for $CO_2$. When a biogas mixture containing both is passed over the adsorbent, methane passes through and is harvested as a methane-rich fraction. Carbon dioxide is adsorbed. To capture the carbon dioxide, gas flow is stopped and the pressure is decreased or even a vacuum applied, which causes the desorption of the carbon dioxide. The desorbed gas may be harvested as a carbon dioxide-rich fraction. A reference describing pressure swing adsorption in detail is Ruthven, Douglas M. et al., 1993, *Pressure Swing Adsorption*, John Wiley & Sons.

Other separation techniques may also be applied, including cryogenic separation. In cryogenic separation gases are distilled at low temperatures and high pressures by differences in their freezing or boiling points. Membrane separation is another technique that can be applied to separate methane and $CO_2$. In membrane separation gases are separated based on differences in their permeation rates through a polymer membrane. Gas separation systems are available from Universal Industrial Gases, Eaton, Pa., and from Air Products and Chemicals, Inc., Allentown, Pa.

The same techniques can also be used to remove oxygen from a hydrocarbon combustion exhaust gas to produce a $CO_2$-rich anaerobic exhaust gas fraction. In addition, oxygen can be removed biologically, by, for instance, passing the combustion exhaust gas into a sealed fermenter containing facultative aerobic microorganisms, a reduced carbon substrate, and the necessary nutrients for the microorganisms. The facultative aerobic microorganisms can consume the oxygen to create the $CO_2$-rich anaerobic exhaust gas fraction, which is then passed into a more strictly anaerobic digester containing methanogenic microorganisms.

If biogas is fractionated into a methane-rich fraction 33 and a carbon dioxide-rich fraction 32, the carbon dioxide-rich fraction 32 may be vented or may be recirculated into the fermentation mixture 10 in the anaerobic digester 11 to serve as a substrate for more methane production, as shown in FIG. 2. The $CO_2$-rich fraction 32 from the biogas may be added to the fermentation mixture instead of or in addition to the $CO_2$-rich combustion exhaust fraction 12.

The produced biogas or the methane-enriched fraction of the biogas may be used for energy. It can, for instance, be burned directly for heat or to produce electricity (e.g., by driving turbines). It can be converted to a liquid fuel by first converting methane to synthesis gas comprising CO and $H_2$ by partial oxidation or by steam reforming or by $CO_2$ reforming. These methods are discussed further below. Synthesis gas can then be converted by catalysts to methanol, ethanol, higher alcohols, or diesel fuel.

The hydrocarbon fuel for the combustion process to produce the exhaust gas may be any suitable fuel, including coal, oil, and natural gas. The methods described herein are particularly suitable for use with coal burning, since coal is a carbon-rich fuel that produces more $CO_2$ than other fuels. The hydrocarbon fuel may also be biogas methane. Thus, the methane produced in the fermentation may be burned to produce a $CO_2$-rich exhaust gas, and the $CO_2$-rich exhaust gas recirculated into the anaerobic digester to serve as a substrate for more methane production.

Fractionating the biogas into a methane-rich fraction and a $CO_2$-rich fraction, and recirculating the $CO_2$-rich fraction, also allows enriching the fermentation mixture for $CO_2$ without adding carbon dioxide from a hydrocarbon combustion exhaust gas. Thus, one embodiment of the invention provides a method of producing alcohol comprising: (a) fermenting organic material in a fermentation mixture to a biogas comprising methane and $CO_2$; (b) fractionating the biogas into a methane-rich fraction and a $CO_2$-rich fraction; (c) converting at least a portion of the methane-rich fraction to synthesis gas comprising CO and $H_2$; (d) contacting the synthesis gas with a catalyst to produce alcohol (or diesel fuel); and (e) recirculating at least a portion of the $CO_2$-rich fraction to the fermentation mixture to enhance biogas methane production.

FIG. 4 is a schematic diagram of the steps in production of alcohol from biogas or a methane-rich fraction of the biogas. Methane in biogas or a methane-rich fraction of biogas is passed through a converter unit 41, which may be a partial oxidation unit or a steam reformer, and is thereby converted to a synthesis gas containing CO and $H_2$. The converter unit may also be or include a dry reformer that reacts $CO_2$ with $CH_4$ to form CO and $H_2$. The CO and $H_2$ are contacted with a catalyst 42 to produce alcohol, which is harvested.

Methods of partial oxidation are well known, and units for partial oxidation of methane to CO and $H_2$ are commercially available. For instance, partial oxidation can be accomplished by oxygen-starved burning. Steam reforming involves the reaction of methane with water vapor at high temperatures and pressures to produce CO and $H_2$. Steam reformers, like partial oxidation units, are commercially available.

In some embodiments of the methods of the invention to produce alcohol or diesel fuel, the method involves partially oxidizing the biogas. This increases the ratio of CO to $H_2$ in the syngas as compared to steam reforming the biogas. Partial oxidation of methane produces a ratio of $2H_2$ per CO. Steam reforming produces a ratio of $3H_2$ per CO. The increased CO to $H_2$ ratio from partial oxidation may decrease the amount of methanol and increase the amount of ethanol and higher alcohols produced from the syngas. In some embodiments, the methods include steam reforming the methane ($H_2O+CH_4 \rightarrow CO+3H_2$). In some embodiments, the methods include $CO_2$ reforming the methane ($CO_2+CH_4 \rightarrow 2CO+2H_2$). In some embodiments, the methods include a combination of steam reforming and $CO_2$ reforming.

Fuel alcohol preferably is predominantly higher alcohols. Alcohol mixtures that are too rich in methanol are sensitive to phase separation in the presence of water, which is ubiquitous in gasoline systems. Thus, preferably the alcohol products are rich in $C_2+$ alcohols and have low methanol content. In some embodiments the alcohol comprises less than 5% methanol by weight. Preferably the alcohol comprises at least 70% by weight $C_2+$ alcohols. In some embodiments, the alcohol comprises less than 0.5% by weight methanol. In some embodiments, the alcohol comprises at least 60% by weight ethanol. In some embodiments the alcohol comprises less than 0.5% by weight methanol and at least 60% by weight ethanol. In some embodiments, the alcohol comprises at least 92.1% by weight ethanol. In some embodiments, the alcohol comprises at least 5% or at least 10% by weight $C_3+$ alcohols.

Several factors can contribute to obtaining alcohol with a high $C_2+$ alcohol content. One is use of a syngas having a higher ratio of CO to $H_2$. As discussed above, partial oxidation of methane produces a higher CO:$H_2$ ratio than steam reforming.

Another factor involved in obtaining alcohol with a high $C_2+$ alcohol content. is using a catalyst and reaction conditions that promote $C_2+$ alcohol formation over methanol formation. Suitable catalysts include the catalysts described in Bao, J. et al., 2003, *Chem. Commun.* 2003:746-747; U.S. Pat. No. 4,235,801; and U.S. Pat. No. 4,333,852. The catalyst described in Bao et al. is a K—Co—Mo/C catalyst. It is formed by the following procedure. $Co(NO_3)_2$ and $(NH_4)_6Mo_7O_{24}$ aqueous solutions are prepared and mixed at a Co/Mo molar ratio of 0.5. Citric acid is added to the solution under constant stirring (citric acid/metallic ions molar ratio=0.1). Then a $K_2CO_3$ solution is dripped slowly into the solution (K/Mo molar ratio=0.1). The pH value of the solution is adjusted to 3.5 with HCOOH and $NH_4OH$. The solution is kept in a water bath at 65° C. until the solution becomes a gel. The gel is dried at 120° C. for 15 hours and calcined in argon at 400° C. for 4 hours. Suitable reaction conditions with the synthesis gas are a temperature of 230° C., a pressure of 6.0 MPa, and a gas hour space velocity of 9600 $hour^{-1}$. Under these conditions, the CO conversion was 7.5% C, the alcohol selectivity was 60.4% of carbon, the alcohol space-time yield was 296 g per kg-hour, and the $C_2+$ alcohol to methanol ratio was 1.48. (Bao, J. et al., 2003, *Chem. Commun.* 2003:746-747.)

Other suitable catalysts are described in U.S. Pat. No. 4,333,852. The catalysts are ruthenium catalysts with a halogen promoter and a phosphine oxide compound as a solvent. An example of catalyst preparation and alcohol synthesis involves the following procedure. 16 milligrams of Ru atoms as triruthenium dodecacarbonyl, 5.6 mmoles of elemental iodine, and 75 ml of tripropylphosphine oxide are placed in a back-mixed autoclave with a net volume of 128 ml and heated with stirring to 55° C. The reactor is pressurized to 500 psi with CO, heated to 240° C., and then pressurized with a $H_2$/CO mixture ($H_2$/CO ratio=2.0) to 6,000 psi. As the reaction proceeds the pressure drops. When it drops to 500 psi, the reactor is repressurized with the synthesis gas to 6,000 psi. With this procedure, ethanol is produced at a rate of 2.05 moles/liter/hour at a selectivity of 50 weight percent. The ethanol plus methanol selectivity is 74 weight percent.

Perhaps the most important mechanism to obtain alcohol with low methanol content and high $C_2+$ alcohol content is to fractionate the alcohol as it is formed into a $C_2+$-rich alcohol fraction and a methanol-rich fraction, harvest the $C_2+$-rich alcohol fraction, and recirculate the methanol-rich fraction into the synthesis gas for contact with the catalyst. Adding methanol to the synthesis gas reaction on the catalyst forces the equilibrium of the $CO+2H_2 \rightarrow CH_3OH$ reaction to the left (Gavin, D. G. and Richard, D. G., European Patent Application 0 253 540). With the equilibrium preventing further net formation of methanol, the CO and $H_2$ react to form ethanol and other $C_2+$ products. Recirculated methanol can also be a reactant for formation of $C_2+$ products by reaction with CO, $H_2$, and/or a second molecule of methanol. If all methanol produced is recirculated, there is no net production of methanol.

In the methanol-recirculation process, the alcohol products from the catalyst are fractionated into a $C_2+$-rich alcohol fraction and a methanol-rich fraction. This is preferably done by condensing the $C_2+$ alcohols from the product mixture at a temperature and pressure below the boiling point of the $C_2+$ alcohols and above the boiling point of methanol. The gaseous methanol-rich fraction is then mixed with the synthesis gas for contact with the catalyst.

The alcohols produced in the methods of the invention, including the $C_2+$-rich alcohol fraction separated from the methanol-rich fraction, can be further processed or fractionated. For instance, ethanol can be separated from other alcohols and other components in the mixtures. The mixtures often contain propanol, butanol, and isobutanol, which can be purified. Acetaldehyde, acetic acid, acetic anhydride, and other components may be present in the alcohol mixtures and can be purified or separated from the alcohols.

In some embodiments of the invention, the catalyst is a sulfided, nanosized transition metal catalyst selected from Group VI metals. In some embodiments, the catalyst is a sulfided, nanosized molybdenum catalyst. (U.S. Pat. No. 6,248,796.)

In some embodiments, the sulfided, nanosized transition metal catalyst is suspended in a solvent, e.g., heavy machine oil, and the synthesis gas is contacted with the catalyst at a temperature in the range of 250-325° C. and at a pressure in the range of 500 to 3000 psi.

The catalyst can also be other metal or inorganic catalysts, such as are disclosed in U.S. Pat. Nos. 4,675,344; 4,749,724; 4,752,622; 4,752,623; and 4,762,858.

Preferably, the catalyst is sulfur-free, because a sulfur-containing catalyst leaches sulfur into the alcohol mixtures it produces. Sulfhydryls are undesirable in fuel alcohol because they carry an odor, upon burning they produce sulfur oxides that cause acid rain and human health problems, and they can damage engine parts in internal combustion engines. Thus, preferably the alcohols contain less than 10 ppm sulfur atoms, more preferably less than 1 ppm sulfur atoms. This can be achieved by removing sulfhydryls from biogas before the biogas is converted to synthesis gas, and then using a sulfur-free catalyst for conversion of synthesis gas to alcohol. One method to remove sulfhydryls from biogas is to contact the biogas with a metal cation that binds sulfhydryls, such as $Fe^{2+}$. Another method is to contact the biogas with another type of agent that binds sulfhydryls, such as amine compounds, which may be immobilized on a resin.

Alternatively, sulfhydryls can be removed from the alcohol product. One method to do this is to contact the alcohol with a metal cation that binds sulfhydryls, such as $Fe^{2+}$. Another method is to contact the alcohol with another type of agent that binds sulfhydryls, such as amine compounds, which may be immobilized on a resin.

In particular embodiments of the methods and products of the invention, the alcohol or purified alcohol has less than 10 ppm or less than 1 ppm (by weight) sulfur atoms in sulfhydryl compounds. In other embodiments, the alcohol or purified alcohol has less than 10 ppm or less than 1 ppm sulfur atoms (in any form).

The methods of the invention can also involve contacting the biogas with a sulfur scrubber separate from the $Fe^{2+}$ produced by the iron-reducing organism. The sulfur scrubber may remove one or more of sulfhydryls, $H_2S$, anionic oxidized forms of sulfur (e.g., sulfate and sulfite), and COS.

More details in alcohol production are provided in U.S. patent application Ser. No. 11/137,874, "Ethanol Production from Biological Wastes," which is incorporated by reference.

Fermentation efficiency, i.e., the yield of methane produced from a given amount of organic material, is enhanced when the fermentation mixture includes $Fe^{3+}$ and an iron-reducing microorganism that reduces $Fe^{3+}$ to $Fe^{2+}$ and produces at least one volatile organic acid. An example of this is the microorganism deposited with the American Type Culture Collection under accession number ATCC 55339. Some organic feedstocks will contain adequate $Fe^{3+}$ to be a substrate for the iron-reducing microorganism. Other feedstocks will require supplementing the fermentation mixture with a $Fe^{3+}$ source, such as magnetite.

The $Fe^{2+}$ produced by the microorganism also has the advantage that it binds sulfhydryl compounds to remove them from the biogas. This produces a substantially sulfur-free biogas. This is advantageous because sulfhydryls carry an odor and when burned they produce sulfur oxides that cause acid rain and human health problems. If the biogas is converted to alcohol, having a sulfur-free biogas is also advantageous because it allows the production of a sulfur-free alcohol. Sulfur-free alcohol is more valuable than sulfur-containing alcohol because sulfhydryls in the alcohol carry an odor, when burned they produce sulfur oxides that cause acid rain and human health problems, and sulfyhydryls can damage internal combustion engines.

Use of the iron-reducing microorganism is described in more detail in U.S. patent application Ser. No. 11/137,874, "Ethanol Production from Biological Wastes."

Thus, the methods generally involve processing the biogas containing methane for energy. In one embodiment, this involves converting at least a portion of the biogas to synthesis gas comprising CO and $H_2$, and contacting the synthesis gas with a catalyst to produce alcohol.

In another embodiment, processing the biogas for energy involves burning a first portion of the biogas for heat or to produce electricity; and converting a second portion of the biogas to synthesis gas comprising CO and $H_2$, and contacting the synthesis gas with a catalyst to produce alcohol. In a more specific embodiment, the second portion of the biogas is a fixed amount of biogas per unit time, and the first portion of a biogas is a variable amount of biogas per unit time (e.g., the remainder).

In the methods of the invention feeding a $CO_2$-rich combustion exhaust or a $CO_2$-enriched fraction from biogas to a fermentation mixture to enhance methane production and anaerobic fermentation efficiency, and to reduce at least some of the $CO_2$ to methane, not all of the $CO_2$ is reduced to methane unless hydrogen is also added as a substrate. Thus, in many embodiments, some $CO_2$ is necessarily produced by the fermentation. This may be released into the atmosphere. But in some embodiments, all or some of this residual $CO_2$ is captured to prevent its release into the atmosphere. The capture can be by pumping the $CO_2$ into a sealed underground reservoir. The capture can also be by adding to the fermentation mixture a source of a cation, e.g., $Ca^{2+}$, that precipitates carbonate to precipitate a portion of the $CO_2$ fed to the fermentation mixture as a carbonate. The source of the cation may be a base, such as calcium hydroxide. This may be useful also to neutralize acidity in the fermentation mixture. Carbon dioxide forms carbonic acid in water, and this may acidify the fermentation mixture, requiring the addition of a base to neutralize it. Acid-forming bacteria may also acidify the fermentation mixture.

A cation source that precipitates carbonate may be added during biogas production along with $CO_2$ in an appropriate ratio with $CO_2$ to allow an elevation in $CO_2$ concentration that enhances biogas production, while still capturing excess $CO_2$ that would otherwise be vented. But, in some embodiments, the $CO_2$ precipitation phase is separated from the biogas production phase. Thus, in some embodiments, biogas production occurs in an anaerobic digester, after a period of biogas production in the anaerobic digester the fermentation mixture is transferred to precipitation tank, and the step of feeding a source of a cation that precipitates carbonate to precipitate a portion of the $CO_2$ fed to the fermentation mixture as a carbonate occurs in the precipitation tank.

The invention will now be illustrated by the following examples, which are intended to illustrate the invention but not limit the scope of embodiments of the invention.

EXAMPLES

Example 1

Comparison of Biogas Production in Batch Mode in Cultures Sparged with $CO_2$ vs. $N_2$ Four 6-gallon carboys are used. Each carboy contains 6 L of distilled water and 48 g of dried nutrient broth (Difco Laboratories Part #0003-17-8, Bacto Beef Extract/Bacto Peptone). The dried nutrient broth is allowed to dissolve overnight without stirring or beating. After 14 hours, 4.2 g of magnetite, 1 mL of ATCC 55339 innoculant (cultured in NBY medium, ATCC medium 815 anaerobically at 25° C.) and 100 g of spent dairy manure from a methane-producing anaerobic reactor is added.

The reactor design is shown in FIG. 5. Carboy or digester 11 contains liquid phase fermentation mixture 10 and a gas phase head space 43. $CO_2$ or $N_2$ sparges the liquid phase 10 through gas sparging tube 20. A sealed clamp 44 is used to seal off the sparging tube 20 after gas sparging is completed. Gas can be collected through a gas sample port 21. The gas passing through port 21 is collected in a Tedlar gas sample bag 41. A clamp 42 is opened when gas collection is desired and closed at other times.

Each reactor is sparged (through the liquid phase) with its selected gas ($CO_2$ or $N_2$) for 5 minutes at 4 psi, with the gas sample port tubing 21 open to air and the gas sample bag 41 removed. Once sparging is complete, the clamp 44 is closed to seal the sparging tube 20, clamp 42 is closed. Then an empty Tedlar gas sample bag 41 is attached, and the sample tubing clamp 42 is opened. Two reactors were sparged with bottled $CO_2$, and 2 with bottled $N_2$. All four reactors are wrapped an electric blanket to heat the liquid phase 35° C.

Analysis: GC analysis is done on an HP 5890 Series II gas chromatograph, using the thermal conductivity detector (TCD). The column is an HP-PLOT/Q (polystyrene-divinyl-benzene stationary phase, part #19095P-Q04), and helium is used as the carrier gas. The GC protocol is based on Agilent Application Note 228-387 ("GC/TCD Analysis of a Natural Gas Sample on a Single HP-PLOT Q Column") an ASTM Standard D1945-96 ("Analysis of Natural Gas"). Each day, prior to running samples, a natural gas standard (Agilent Part #5080-8756) is run to verify the instrument calibration. If there is any concern about the identity of a peak, the sample is spiked with the gas standard and re-run. The GC can quantitatively identify nitrogen, methane, carbon dioxide, ethane, propane, iso-butane, n-butane, iso-pentane and n-pentane.

Results:

Carbon dioxide from the head space of the reactors sparged with CO2 is taken up into the liquid phase, as shown by development of a partial vacuum in the head space. This is evidenced by liquid climbing up sparging tube 20 and sample bag 41 collapsing to a smaller volume under vacuum.

More total methane is produced over the course of the digestion in batch reactors that are sparged with $CO_2$ than those that are sparged with $N_2$ initially. This indicates that $CO_2$ addition stimulates methane production and that some of the added $CO_2$ is reduced to methane by the microorganisms in the digestion.

Example 2

Continuous Addition of $CO_2$

Anaerobic digestion mixtures in four carboys are set up as described in Example 1 with nitrogen head space. Dissolved $CO_2$ is measured in the liquid phase with a Orion5-Star 1119000 carbon dioxide electrode from Thermo Scientific and Orion instruments. When significant biogas production is observed to begin, the dissolved $CO_2$ concentration is measured in the carboys. Digestion is allowed to continue in two control carboys without any gas sparging. In the other two carboys, pure anaerobic $CO_2$ is sparged into the liquid mixture at a rate sufficient to increase the dissolved $CO_2$ concentration at least 5 mM above the dissolved concentration in the control digesters. The pH is monitored in all four carboys, and acid or base is added as needed to maintain a pH in the range of 6.8 to 8.0. Biogas produced in all four carboys is collected throughout the digestion and the composition of the biogas is measured to determine total methane produced. Digestion is continued in each carboy until the rate of methane production slows substantially. At that point, the digestion is stopped and volatile organic solids in the digester are measured to determine the amount of organic matter that has not been converted into biogas. Volatile organics are determined by drying a representative mixed sample at 105° C. and then heating to 550° C. for 24 hours and measuring the mass difference after heating to 550° C. for 24 hours. Volatile organics are measured at the beginning and end of the digestion. The atomic composition of the volatile organics is also measured at the beginning and end of the digestion.

Results:

The total amount of methane produced over the course of the digestion is greater in the digesters that are sparged with $CO_2$. The moles of carbon from volatile organics gasified is determined by the difference in volatile organics between the beginning and end of the digestion in each digester and the atomic composition of the volatile organics. By mass balance of moles methane produced minus moles volatile organics carbon consumed, it is determined that some added $CO_2$ is converted to methane in the experimental digesters sparged with $CO_2$.

All patents, patent documents, and other references cited are hereby incorporated by reference.

What is claimed is:

1. A method of producing methane comprising:
   collecting combustion exhaust gas from a hydrocarbon fuel combustion process;
   separating $O_2$ from $CO_2$ in the exhaust gas to generate a $CO_2$-rich anaerobic exhaust gas fraction;
   feeding the $CO_2$-rich anaerobic exhaust gas fraction to a fermentation mixture containing methanogenic microorganisms;
   feeding a reduced substrate selected from the group consisting of $H_2$ and organic material and a combination thereof, to the fermentation mixture; and
   producing a biogas comprising methane in the fermentation mixture by the anaerobic fermentation of methanogenic microorganisms;
   fractionating the biogas into a methane-rich fraction and a carbon dioxide-rich fraction; and
   processing the methane-rich fraction for energy;
   wherein feeding the $CO_2$-rich anaerobic exhaust gas fraction to the fermentation mixture increases methane production in the fermentation mixture.

2. The method of claim 1 further comprising recirculating at least a portion of the carbon dioxide-rich fraction into the fermentation mixture.

3. A method of producing methane and alcohol/alcohols comprising:
   collecting combustion exhaust gas from a hydrocarbon fuel combustion process;
   separating $O_2$ from $CO_2$ in the exhaust gas to generate a $CO_2$-rich anaerobic exhaust gas fraction;
   feeding the $CO_2$-rich anaerobic exhaust gas fraction to a fermentation mixture containing methanogenic microorganisms;
   feeding a reduced substrate selected from the group consisting of $H_2$ and organic material and a combination thereof, to the fermentation mixture; and
   producing a biogas comprising methane in the fermentation mixture by the anaerobic fermentation of methanogenic microorganisms;
   converting at least a portion of the biogas to synthesis gas comprising CO and $H_2$; and
   contacting the synthesis gas with a catalyst to produce alcohol;
   wherein feeding the $CO_2$-rich anaerobic exhaust gas fraction to the fermentation mixture increases methane production in the fermentation mixture.

4. A method of producing methane and alcohol/alcohols comprising:
   collecting combustion exhaust gas from a hydrocarbon fuel combustion process;
   separating $O_2$ from $CO_2$ in the exhaust gas to generate a $CO_2$-rich anaerobic exhaust gas fraction;
   feeding the $CO_2$-rich anaerobic exhaust gas fraction to a fermentation mixture containing methanogenic microorganisms;
   feeding a reduced substrate selected from the group consisting of $H_2$ and organic material and a combination thereof, to the fermentation mixture; and
   producing a biogas comprising methane in the fermentation mixture by the anaerobic fermentation of methanogenic microorganisms;
   burning a first portion of the biogas for heat or to produce electricity; and
   converting a second portion of the biogas to synthesis gas comprising CO and $H_2$; and contacting the synthesis gas with a catalyst to produce alcohol;

wherein feeding the $CO_2$-rich anaerobic exhaust gas fraction to the fermentation mixture increases methane production in the fermentation mixture.

5. The method of claim 4 wherein the second portion of the biogas is a fixed amount of biogas per unit time, and the first portion of biogas is a variable amount of biogas per unit time.

6. The method of claim 4 further comprising purifying the alcohol, wherein the purified alcohol comprises less than 10 ppm sulfur atoms, less than 5% methanol, and at least 70% $C_2$+ alcohols by weight.

7. The method of claim 6 wherein the catalyst is sulfur-free; the reduced substrate is organic material that contains sulfur;

the fermentation mixture includes $Fe^{3+}$ ions and a microorganism that reduces $Fe^{3+}$ and produces at least one volatile organic acid from organic substrates; and the method further comprises removing sulfhydryls from the biogas by contacting the biogas with $Fe^{2+}$ formed by reduction of $Fe^{3+}$ in the anaerobic digester by the microorganism that reduces $Fe^{3+}$ and produces at least one volatile organic acid from organic substrates.

* * * * *